United States Patent
Ko et al.

(10) Patent No.: US 10,456,050 B2
(45) Date of Patent: Oct. 29, 2019

(54) FERROELECTRIC COMPOSITE MATERIAL-BASED ARTIFICIAL ELECTRONIC SKIN

(71) Applicant: UNIST(ULSAN NATIONAL INSTITUTE OF SCIENCE AND TECHNOLOGY), Ulsan (KR)

(72) Inventors: Hyunhyub Ko, Ulsan (KR); Jonghwa Park, Ulsan (KR); Heon Sang Lee, Ulsan (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 164 days.

(21) Appl. No.: 15/570,449

(22) PCT Filed: Nov. 11, 2015

(86) PCT No.: PCT/KR2015/012107
§ 371 (c)(1),
(2) Date: Oct. 30, 2017

(87) PCT Pub. No.: WO2017/043695
PCT Pub. Date: Mar. 16, 2017

(65) Prior Publication Data
US 2018/0140207 A1    May 24, 2018

(30) Foreign Application Priority Data
Sep. 7, 2015  (KR) ........................ 10-2015-0126515

(51) Int. Cl.
| | |
|---|---|
| *A61B 5/0205* | (2006.01) |
| *A61L 27/26* | (2006.01) |
| *A61F 2/10* | (2006.01) |
| *A61B 5/01* | (2006.01) |
| *A61B 5/024* | (2006.01) |

(Continued)

(52) U.S. Cl.
CPC ............ *A61B 5/02055* (2013.01); *A61B 5/01* (2013.01); *A61B 5/024* (2013.01); *A61B 5/053* (2013.01);

(Continued)

(58) Field of Classification Search
CPC ....... A61B 5/01; A61B 5/02055; A61B 5/024; A61B 5/02438; A61B 5/053; A61L 27/60
See application file for complete search history.

(56) References Cited

FOREIGN PATENT DOCUMENTS

KR         10-1449410 B1    10/2014

OTHER PUBLICATIONS

International Search Report issued in PCT/KR2015/012107; dated Jul. 1, 2016.

(Continued)

*Primary Examiner* — Christine H Matthews
(74) *Attorney, Agent, or Firm* — Studebaker & Brackett PC

(57) ABSTRACT

An artificial electronic skin according to the present disclosure comprises: a lower electrode; a first layer laminated on the lower electrode; a first micro dome formed on the first layer in a semispherical shape so as to stand upright upwards; a second layer laminated on the first layer; a second micro dome formed on the lower portion of the second layer, which lies opposite the first layer, in a semispherical shape to be able to engage with the first micro dome; an upper electrode laminated on the upper end surface of the second layer; and a pattern layer laminated on the upper end surface of the upper electrode so as to receive an external pressure applied thereto. The artificial electronic skin according to the present disclosure is advantageous in that a dynamic pressure, a static pressure, and a temperature can be sensed and distinguished by a single element, using different signals.

11 Claims, 26 Drawing Sheets
(26 of 26 Drawing Sheet(s) Filed in Color)

(51) Int. Cl.
- A61B 5/053 (2006.01)
- A61B 5/00 (2006.01)
- A61L 27/40 (2006.01)
- A61L 27/60 (2006.01)

(52) U.S. Cl.
CPC .............. *A61B 5/6824* (2013.01); *A61F 2/10* (2013.01); *A61L 27/26* (2013.01); *A61L 27/40* (2013.01); *A61L 27/60* (2013.01); *A61B 5/02438* (2013.01)

(56) References Cited

OTHER PUBLICATIONS

Park et al.; Giant Tunneling Piezoresistance of Composite Elastomers with Interlocked Microdome Arrays for Ultrasensitive and Multimodal Electronic Skins; ACS NANO; 2014; pp. 4689-4697; vol. 8; No. 5.

Fan et al.; Transparent Triboelectric Nanogenerators and Self-Powered Pressure Sensors based on Micropatterned Plastic Films; Nano Letters; 2012; pp. A-F, 6 pages.

Schwartz et al.; Flexible polymer transistors with high pressure sensitivity for application in electronic skin and health monitoring; Nature Communications; 2013; pp. 1-8; vol. 4.

Wang et al.; Silk-Molded Flexible, Ultrasensitive, and Highly Stable Electronic Skin for Monitoring Human Physiological Signals; Advanced Materials; 2014; pp. 1336-1342; vol. 26.

Yoshioka et al.; Neural Coding Mechanisms Underlying Perceived Roughness of Finely Textured Surfaces; The Journal of Neuroscience; 2001; pp. 6905-6916; vol. 21; No. 17.

Park et al.; Fingertip skin-inspired microstructured ferroelectric skins discriminate static/dynamic pressure and temperature stimuli; Science Advances; Oct. 30, 2015; pp. 1-13.

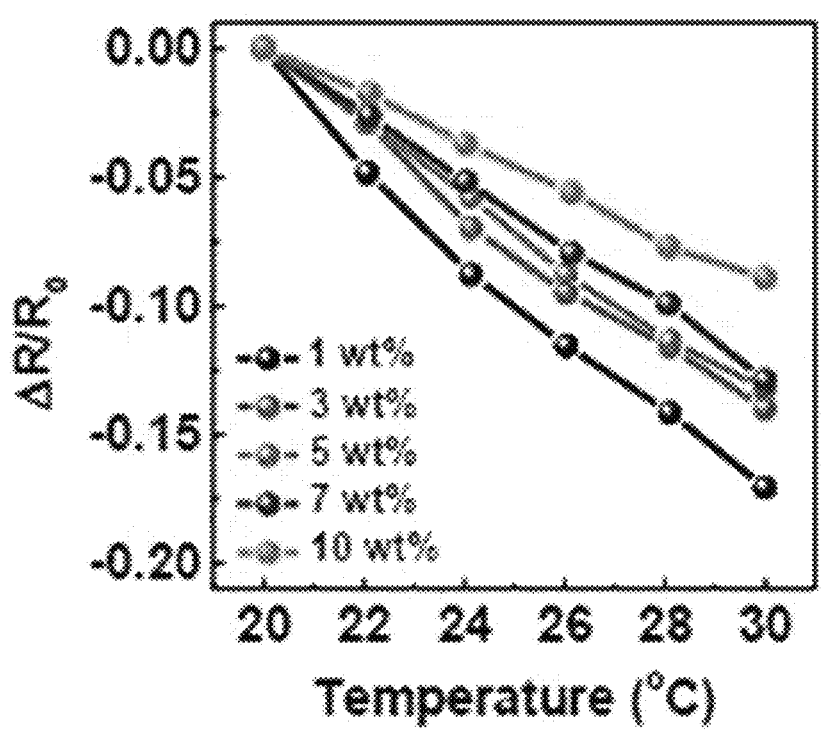

FERROELECTRIC COMPOSITE MATERIAL-BASED ARTIFICIAL ELECTRONIC SKIN

CROSS REFERENCE TO RELATED APPLICATIONS

This application claims the priority of Korean Patent Application No. 10-2015-0126515, filed on Sep. 7,2015 in the Korean Intellectual Property office. Further, this application is a National Phase application of International Application No. PCT/KR 2015/012107 filed on Nov. 11, 2015, which is incorporated herein by reference in its entirety.

TECHNICAL FIELD

The present invention relates to a ferroelectric composite material-based artificial electronic skin, and more particularly, to a ferroelectric composite material-based artificial electronic skin in which a composite material of polyvinylidene fluoride (PVDF) having a ferroelectric property and reduced graphene oxide (rGO) is controlled by an interlocked micro dome structure, wherein a static touch and a temperature may be sensed using a resistance property which changes according to physical and thermal stimuli and conventional dynamic touch sensing based on a piezoelectric property.

In addition, the present invention relates to an application technique of an artificial electronic skin which may monitor a pulse change according to a temperature and distinguish and sense a sound wave and a surface texture by distinguishing and sensing properties of dynamic and static touches and the temperature and introducing a fingerprint simulation pattern.

BACKGROUND ART

A conventional artificial electronic skin has a limitation in simultaneously measuring a static or dynamic touch through a single measurement mode and has difficulty in separating a sensing signal for distinguishing and sensing a physical touch and temperature most of all.

In addition, since pulse signal sensing using the conventional artificial electronic skin cannot include an influence on a temperature and has difficulty in simultaneously measuring static and dynamic touches, it is difficult for the conventional artificial electronic skin to accurately sense a roughness, a texture, or the like of a surface like real skin.

DOCUMENT OF RELATED ART

Patent Document

Korea Patent Registration No. 10-1449410 (registered on Oct. 2, 2014)

DISCLOSURE

Technical Problem

The present invention is directed to providing an artificial electronic skin in which a composite material of polyvinylidene fluoride (PVDF) and reduced graphene oxide (rGO) is controlled by an interlocked micro dome structure, wherein a static touch and a temperature may be distinguished and sensed using a resistance property which changes according to a pressure and the temperature and a dynamic touch sensing property of a conventional piezoelectric material.

Technical Solution

One aspect of the present invention provides an artificial electronic skin including a lower electrode, a first layer laminated on the lower electrode, a hemispherical first micro dome formed on the first layer to stand upright, a second layer laminated on the first layer, a hemispherical second micro dome formed on a lower portion of the second layer, which faces the first layer, to be interlocked with the first micro dome, an upper electrode laminated on an upper end surface of the second layer, and a pattern layer laminated on an upper end surface of the upper electrode and configured to receive an external pressure applied thereto.

Advantageous Effects

An artificial electronic skin according to the present invention can sense and distinguish a dynamic pressure, a static pressure, and a temperature with a single element by using different signals.

In addition, the artificial electronic skin according to the present invention can sense a temperature by using a temperature change property of a composite material of polyvinylidene fluoride (PVDF) and reduced graphene oxide (rGO), and can implement temperature sensitivity through an interlocked dome structure.

DESCRIPTION OF DRAWINGS

The patent or application file contains at least one drawing executed in color. Copies of this patent or patent application publication with color drawing(s) will be provided by the Office upon request and payment of the necessary fee.

FIGS. 2A-2G illustrate diagrams for describing a temperature sensing property of a flexible nanocomposite film of reduced graphene oxide (rGO) and polyvinylidene fluoride (PVDF).

MODES OF THE INVENTION

Figure 1:
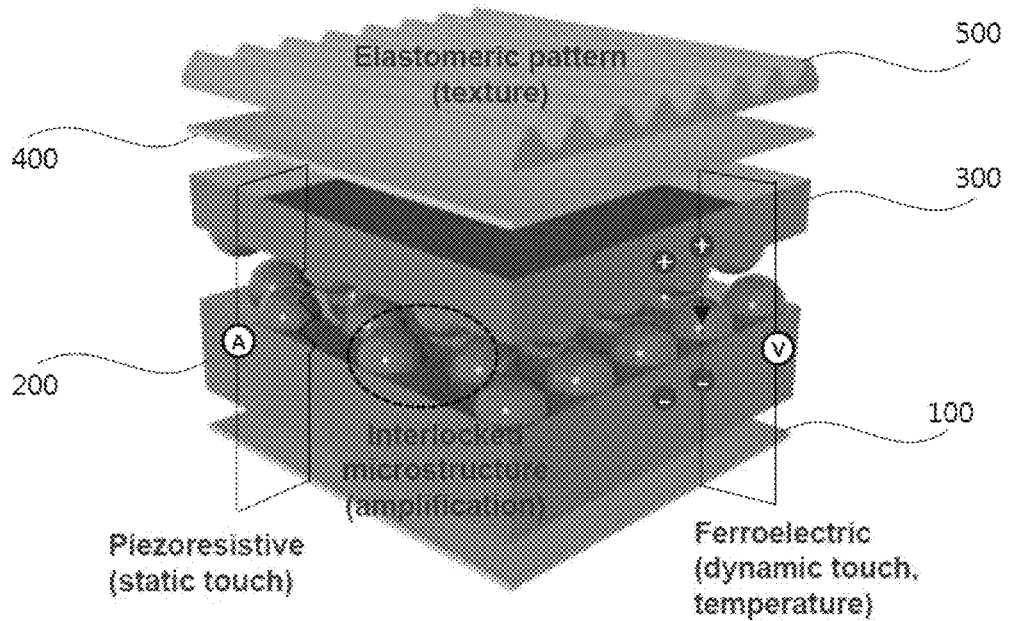
FIG. 1 is a configuration diagram of a multifunctional electronic skin obtained by simulating human skin.

Hereinafter, embodiments of the present invention will be described in detail with reference to the accompanying drawings. Before describing the present invention, terms and words used in this specification and claims should not to be interpreted as limited to commonly used meanings or meanings in dictionaries and should be interpreted as having meanings and concepts which are consistent with the technological scope of the present invention based on the principle that the inventors have appropriately defined concepts of terms in order to describe the present invention in the best way.

Therefore, since the embodiments described in this specification and configurations illustrated in the drawings are only exemplary embodiments and do not represent the overall technological scope of the present invention, it should be understood that the present invention may cover various equivalents, modifications, and substitutions at the time of filing of this application.

FIG. 1 is a configuration diagram of an artificial electronic skin according to the present invention.

As illustrated in FIG. 1, the artificial electronic skin according to the present invention includes a lower electrode 100, a first layer 200, a second layer 300, an upper electrode 400, and a pattern layer 500.

The lower electrode 100 is a copper (Cu) electrode, is laminated on a lowermost portion of the artificial electronic skin according to the present invention, and is used as an electrode for measuring a piezoelectric property and a piezoresistive property.

The first layer 200 is formed by being laminated on the lower electrode 100 and made of a composite material of polyvinylidene fluoride (PVDF) and reduced graphene oxide (rGO) to sense static and dynamic touches, and a temperature.

In this case, a plurality of hemispherical first micro domes 210 are formed at an upper end of the first layer 200. The first micro domes 210 may have an expanded surface area to improve sensitivity with respect to a vertical pressure.

The second layer 300 is formed by being laminated on the first layer 200 and made of a composite material of PVDF and rGO to sense the static and dynamic touches, and the temperature, in the same manner as the first layer 200.

However, it is preferable for a plurality of second micro domes 310 to be formed at a lower end of the second layer 300 to be interlocked with the first micro domes 210 formed at the upper end of the first layer 200.

The upper electrode 400 is laminated on the second layer 300 and used as an electrode for measuring a piezoelectric property and a piezoresistive property, in the same manner as the lower electrode 100.

The pattern layer 500 is made with a fabric having an elastomeric pattern, is configured with a pattern obtained by simulating a fingerprint, and amplifies a signal, thereby implementing an effective transmission of force.

The lower electrode 100 and the upper electrode 400 are adhered to the first layer 200 and the second layer 300, respectively, by a silver paste. The silver paste is annealed at 90° C. for one hour to minimize a contact resistance.

A temperature may be measured via a current value or a voltage value which is measured through wires connected to the lower electrode 100 and the upper electrode 400.

Figure 2A:
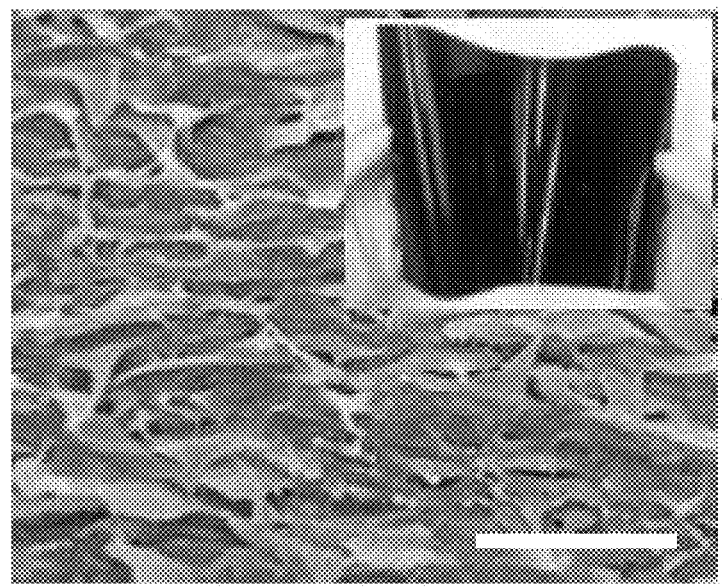
Figure 2B:
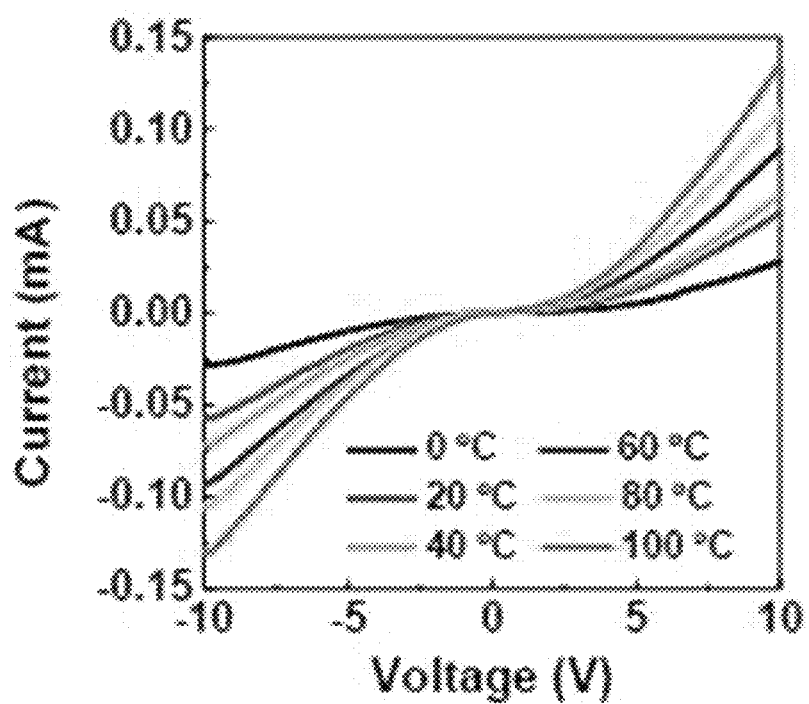

As illustrated in FIGS. 2A-2G, it can be seen that a current increases as the temperature increases from 0° C. to 100° C. (FIG. 2B).

On the other hand, as illustrated in FIG. 2C, it can be seen that a resistance decreases as the temperature increases.

Meanwhile, as illustrated in FIG. 2A, a cross-sectional scanning electron microscope (SEM) image of a composite film of reduced graphene oxide (rGO) and PVDF with an rGO concentration of 1 wt % (weight percent) shows that an rGO sheet is uniformly dispersed and laminated in a PVDF matrix.

Figure 2D:
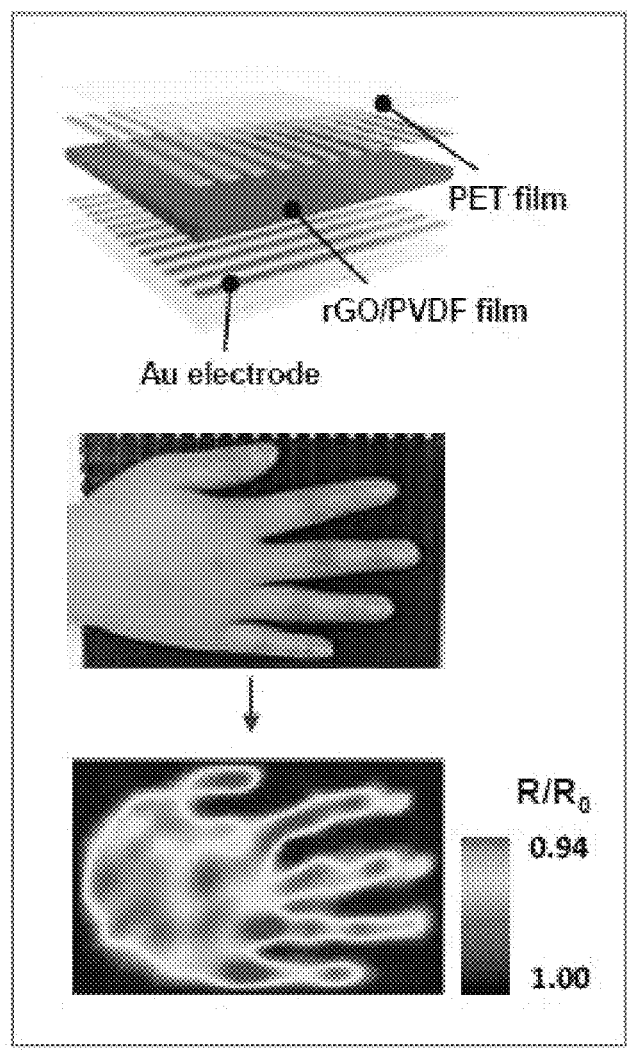

For example, as illustrated in FIG. 2D, when a human hand is placed on the artificial electronic skin according to the present invention, temperature changes over all contact portions are displayed by a temperature sensor.

Figure 2E:
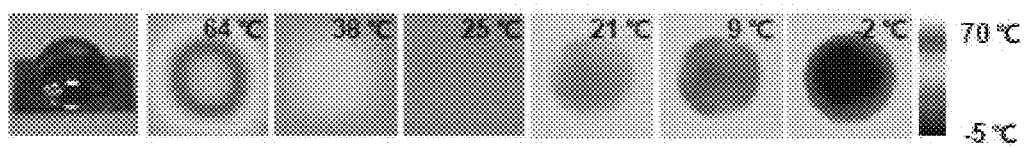

Also, a representative optical image and infrared camera images when water droplets having different temperatures are dropped onto the artificial electronic skin according to the present invention are illustrated in FIG. 2E.

Figure 2F:
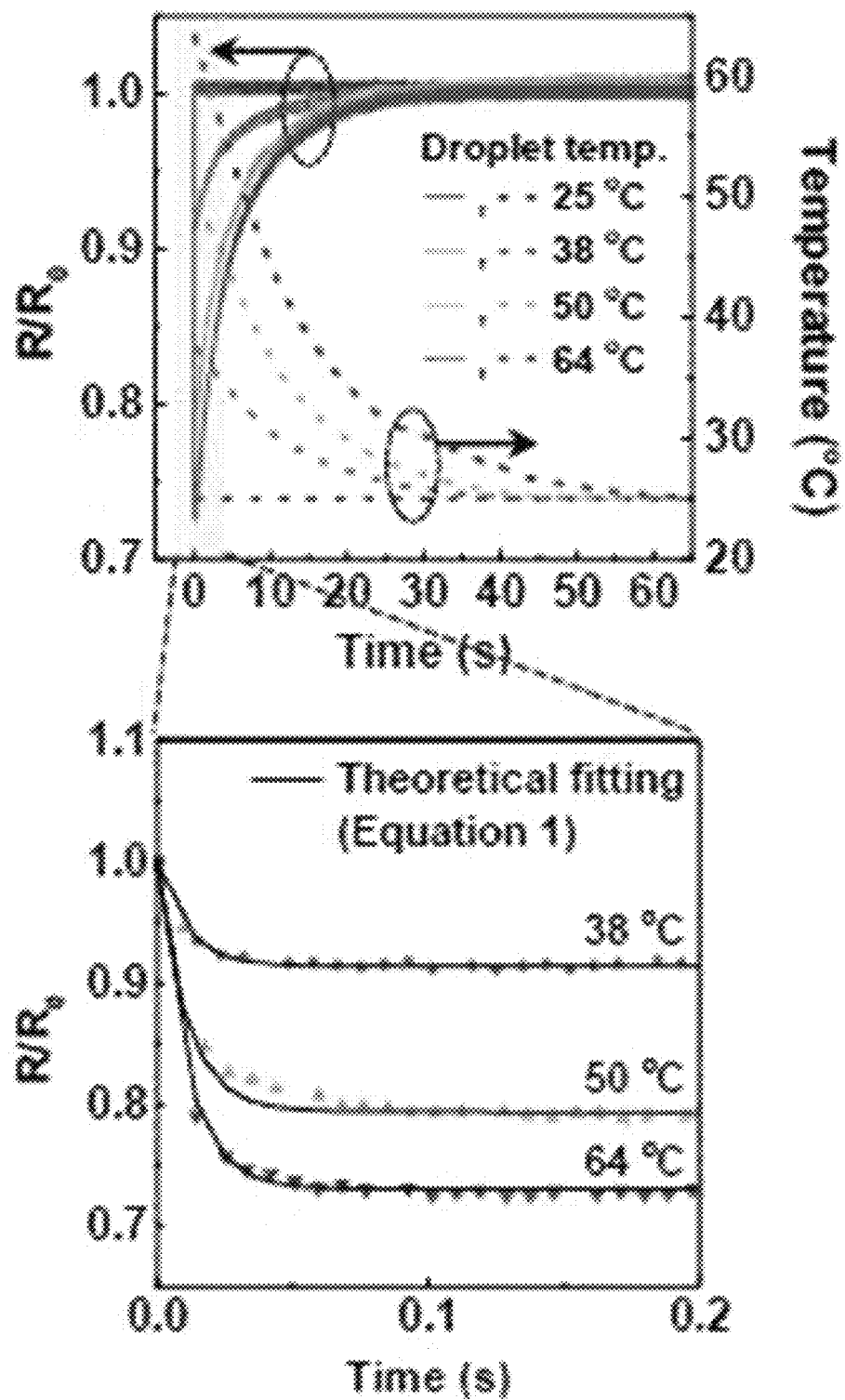

As illustrated in FIGS. 2F and 2H, a solid line shows a time-dependent resistance change of the artificial electronic skin while a dotted line shows a temperature of a water droplet. When water droplets are dropped onto the artificial electronic skin in a space at 25° C., an electrical resistance of the artificial electronic skin does not change.

Figure 2G:
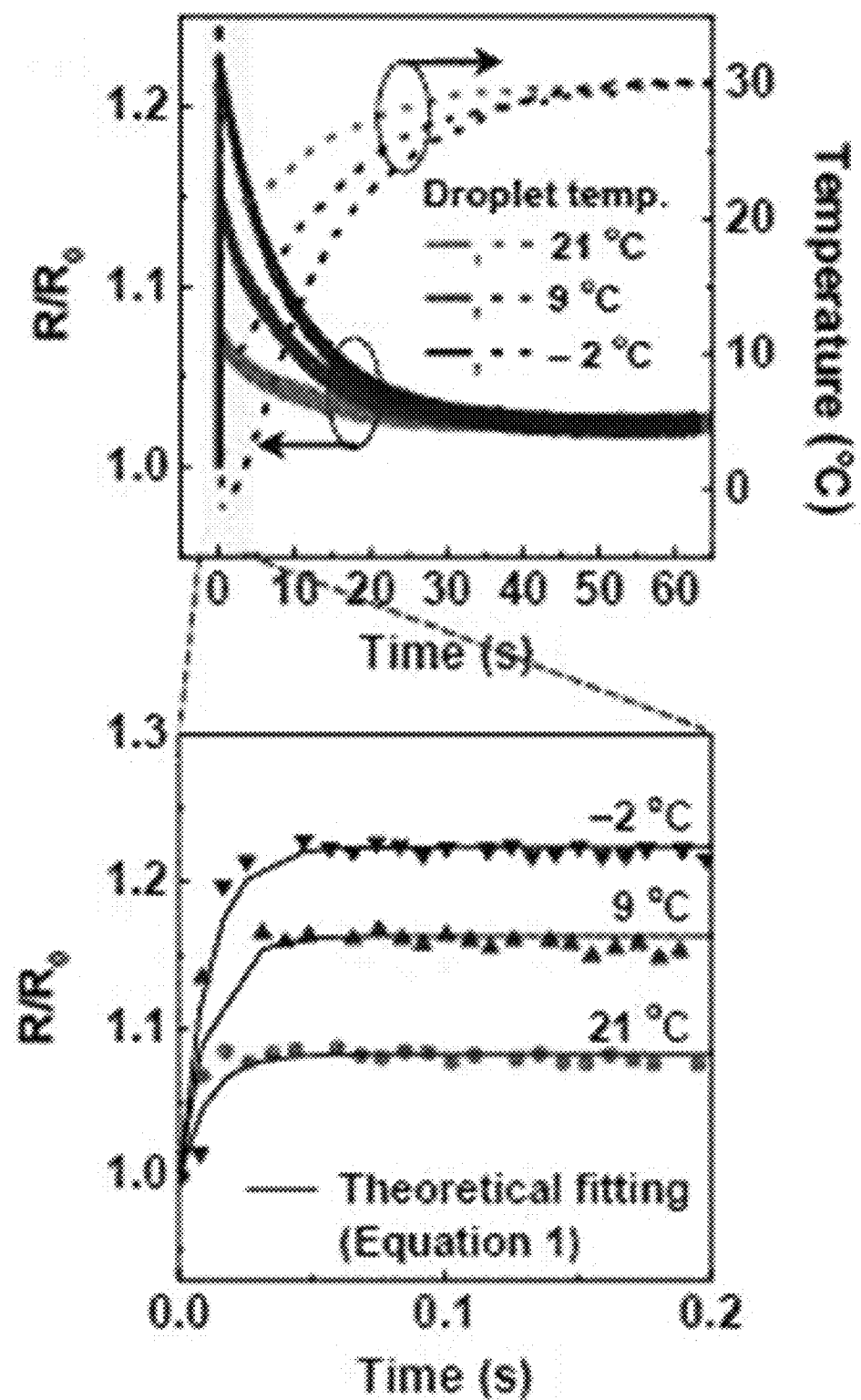

On the other hand, when warm water droplets at 38° C., 50° C., and 64° C. are dropped thereon, a relative resistance thereof instantaneously decreases from 0.74 to 0.92 (FIG. 2F), and, conversely, when cold water droplets are dropped thereon, the relative resistance thereof instantaneously increases (FIG. 2G).

Meanwhile, a pressure-induced electrical property, a piezoelectric resistance, and a piezoelectric signal are measured by using a semiconductor parameter analyzer and a source meter which are connected to the lower electrode 100 and the upper electrode 400 by wires.

A planar composite film is not sensitive to an instantaneous pressure change induced by water droplets on the artificial electronic skin. Therefore, in the present invention, an interlocked structure of a micro dome array may be employed on a sheet composite film to significantly improve pressure sensitivity (FIG. 3A).

Figure 3:
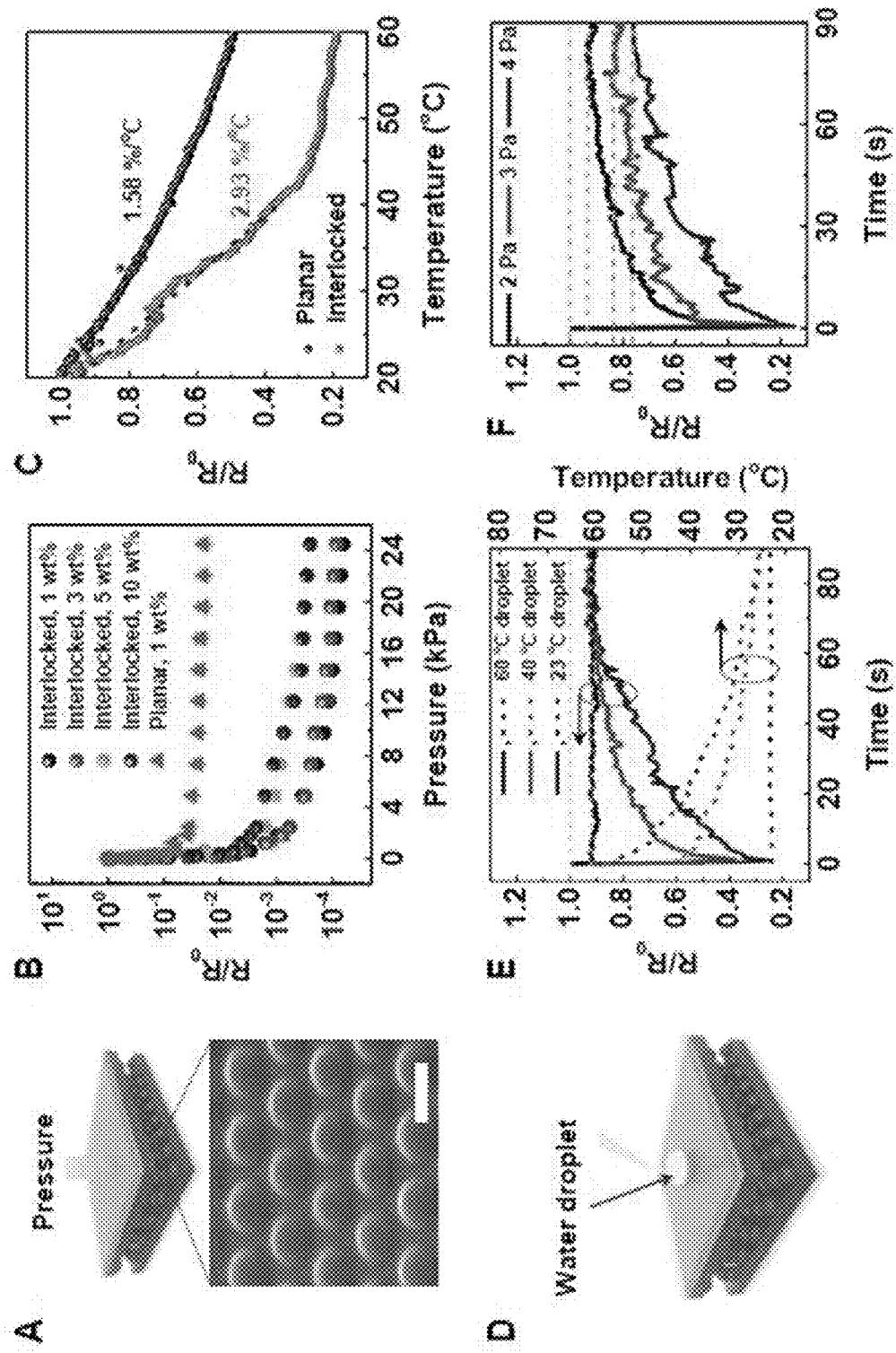
FIG. 3 illustrates diagrams for describing properties of a piezoresistive electronic skin having an interlocked micro dome array to sense stimuli of a static pressure and a temperature.

Pressure sensitivity of the interlocked micro dome array is significantly higher than that of a planar film due to a large change of a contact area between adjacent micro dome arrays and a stress concentration effect (FIG. 3B).

Also, the interlocked structure of the micro dome array has a higher temperature coefficient of resistance (TCR) value (2.93%/° C.) than a TCR value (1.58%/° C.) of a planar film (FIG. 3C).

Meanwhile, in order to evaluate a temporal response of the artificial electronic skin having the interlocked structure according to simultaneous and continuous temperature and pressure changes, time-dependent changes of an electronic skin resistance and a water temperature are analyzed immediately after water droplets are dropped at various temperatures.

The dropping of water droplets onto the electronic skin at room temperature results in a relative resistance decrease to 0.92 due to a pressure applied by the water droplets (FIG. 3E).

When warm water droplets at temperatures of 40° C. and 60° C. are dropped onto the electronic skin, the resistance instantaneously decreases to 0.38 and 0.25, respectively, due to a pyroelectric effect and a piezoresistive effect.

In this case, as time elapses, the resistance gradually increases due to cooling of the warm water droplets, and finally reaches a resistance value of 0.92, which is a thermal equilibrium state corresponding to a static pressure applied by the water droplets.

When a water droplet pressure changes, an equilibrium value of the relative resistance depends on different pressure values (FIG. 3F).

Figure 4A:
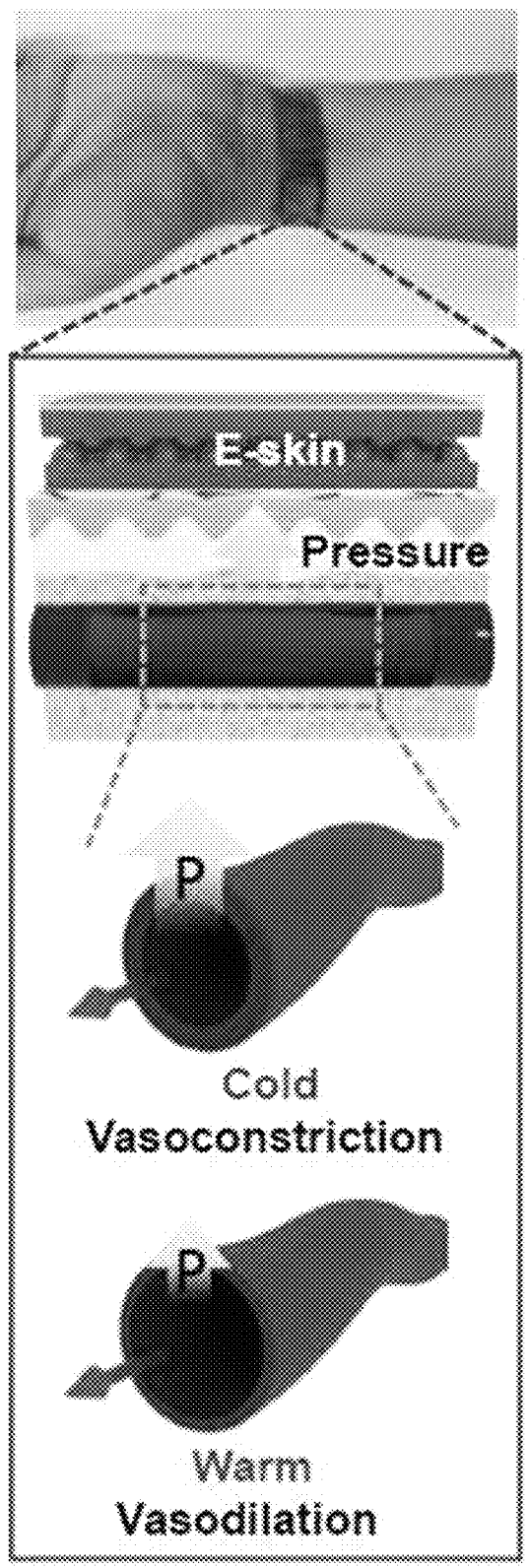
FIGS. 4A-F illustrate diagrams for describing properties of a piezoresistive electronic skin having an interlocked micro dome array to monitor stimuli of an arterial pulse pressure and a temperature.

Meanwhile, as illustrated in FIG. 4A, both surfaces of the artificial electronic skin according to the present invention are encapsulated by a polyimide film with a size of 1 to 2 cm in a wearable manner and the artificial electronic skin is wrapped around a wrist to monitor an arterial pressure pulse.

A change of the arterial pressure pulse and a body temperature are observed after running and exercising for 5 minutes and soaking the wrist in warm and cold water for 2 minutes.

A blood vessel expands or contracts according to a skin temperature by a decrease or increase in a pulse pressure.

Figure 4B:
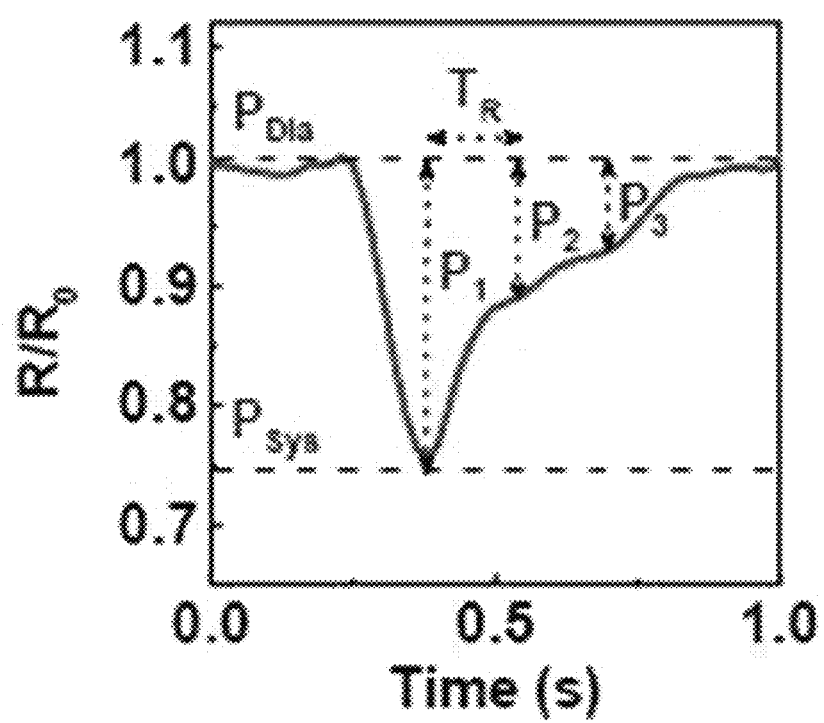

FIG. 4B illustrates a typical piezoelectric resistance readout of a wrist pulse pressure and illustrates three distinguishable peaks $P_1$, $P_2$, and $P_3$. A pulse pressure $P_1$ is a difference between a systolic pressure $P_{Sys}$ and a diastolic blood pressure $P_{Dia}$ due to a blood flow derived by cardiac contraction.

Meanwhile, reflection wave pressures $P_2$ and $P_3$ are generated by waves reflected from peripheral regions ($P_2$ is a hand and $P_3$ is a lower body).

Figure 4C:
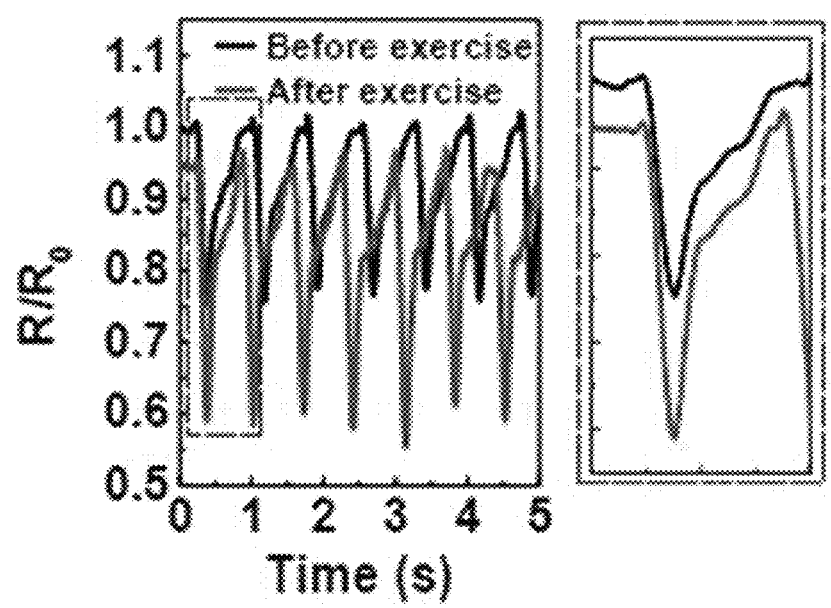

In FIG. 4C, a radial artery augmentation index ($AI_r$) ($P_2/P_1$) and a radial diastolic augmentation index (DAI) ($P_3/P_1$) are observed to be 0.45 and 0.31, respectively, under normal conditions before exercise.

Figure 4D:
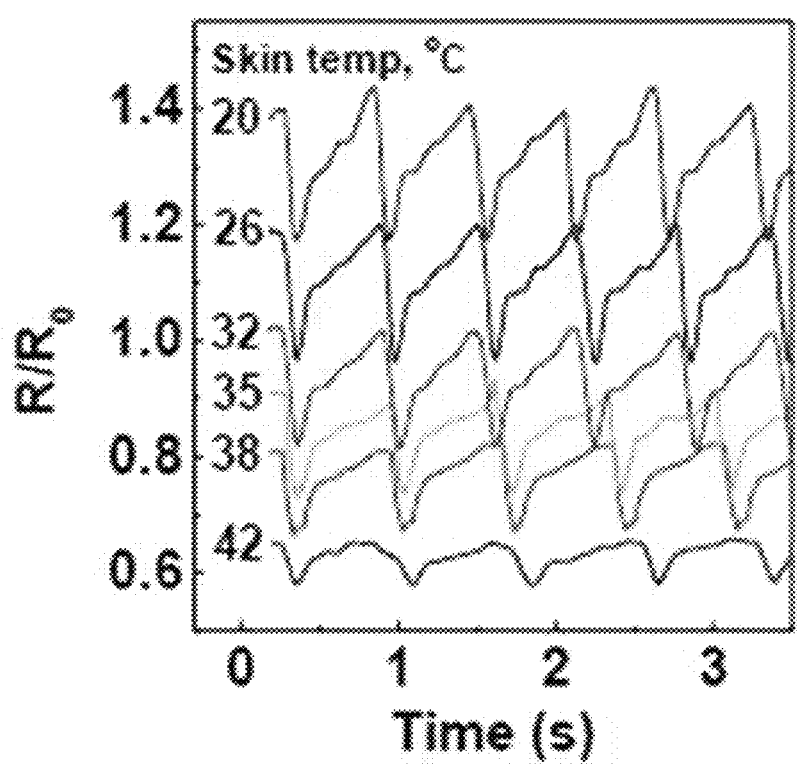
Figure 4E:
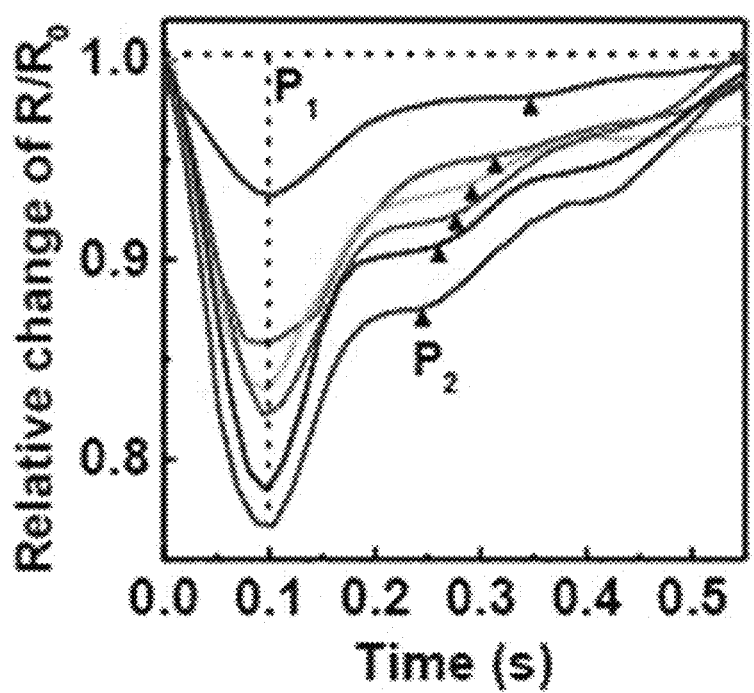

In FIG. 4D, as the skin temperature increases from 20° C. to 42° C., a relative resistance of the diastolic blood pressure $P_{Dia}$ decreases from 1.40 to 0.64. In FIG. 4E, the arterial pressure pulse clearly shows different waveforms according to the temperature.

Here, all of the pulses and the reflection wave pressures $P_1$, $P_2$, and $P_3$ decrease as the temperature increases.

Figure 4F:
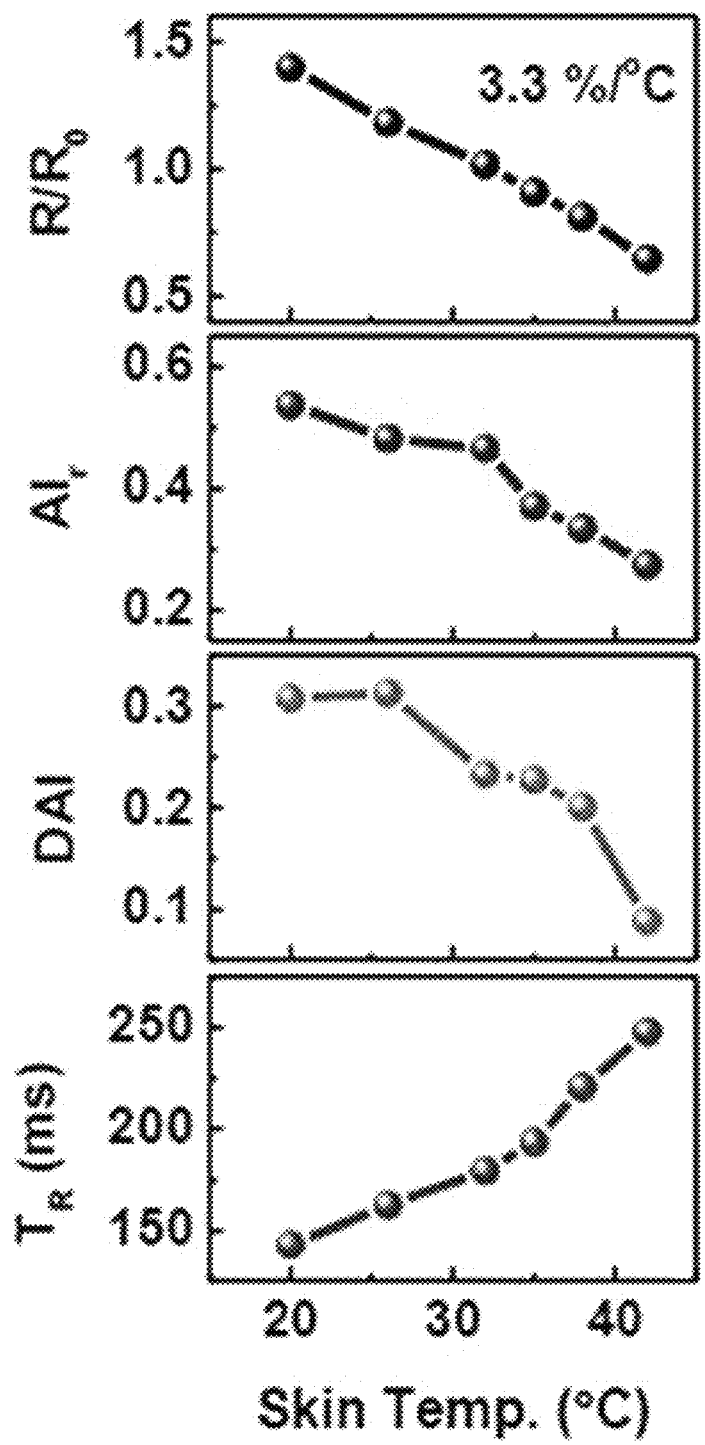

A detailed analysis of parameters in addition to the pulse waveforms is as illustrated in FIG. 4F.

In FIG. 3C, the relative resistance linearly decreases as the skin temperature increases. Such a linear relationship between the resistance and the temperature may be used to directly monitor the skin temperature while measuring the arterial pressure pulse.

The ferroelectric artificial electronic skin having the interlocked structure according to the present invention is capable of piezoelectric recognition of a dynamic touch stimulus.

Figure 5A:
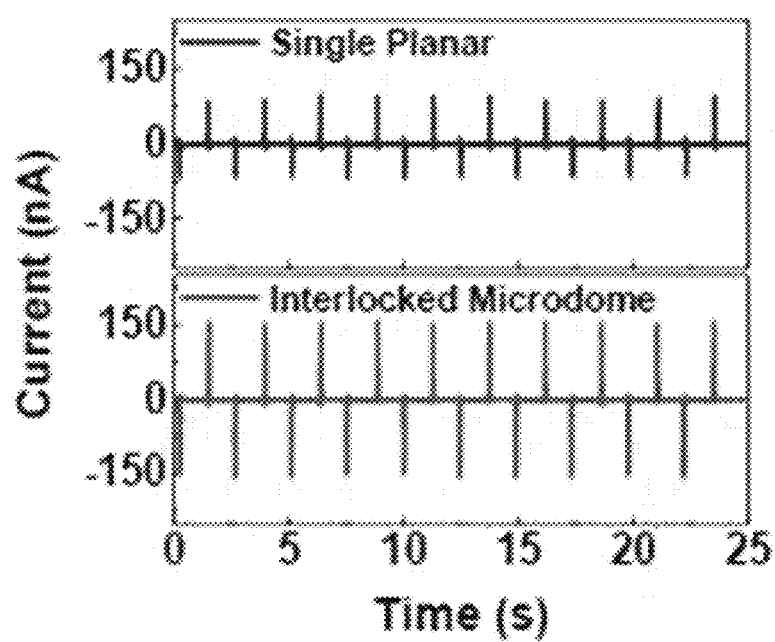
FIGS. 5A-5G illustrate diagrams for describing properties of a piezoelectric electronic skin having an interlocked micro dome array to sense a dynamic touch and an acoustic sound.

In FIG. 5A, when compared to a planar piezoelectric film, since an interlocked electronic skin has a wide contact area and has a pressure concentration effect at a narrow contact area between micro domes, piezoelectric performance thereof may be improved.

Figure 5B:
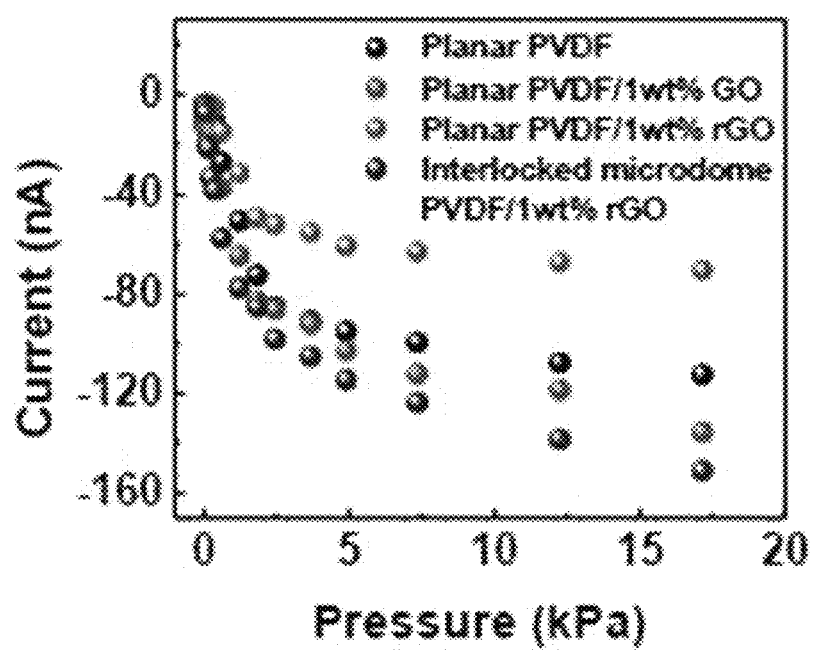

As illustrated in FIG. 5B, a piezoelectric current of an interlocked micro dome film varies according to a general force, which is applied at a sensitivity of 35 uA/Pa at a pressure of 2.45 kPa or less and at a sensitivity of 5 uA/Pa in a pressure range of 2.45 to 17.15 kPa.

Figure 5C:
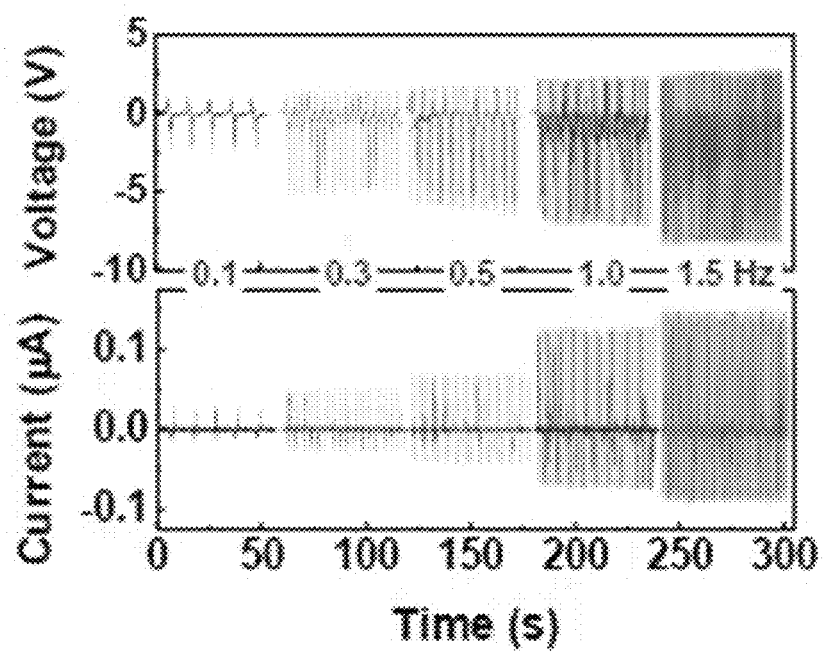

As illustrated in FIG. 5C, a piezoelectric current and voltage gradually increase as an applied impact frequency (a range of 0.1 Hz to 1.5 Hz) increases.

Instantaneous deformation and relaxation after a change of the piezoelectric current of the interlocked micro dome array allow detection of a sound wave composed of high frequency vibration.

Figure 5D:
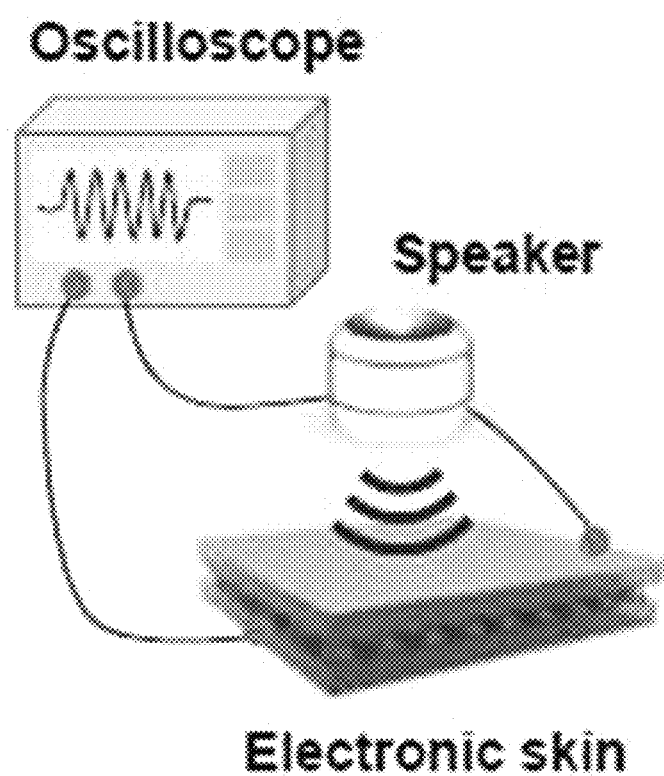

As illustrated in FIG. 5D, as a sound waveform generated from a speaker is monitored by the interlocked electronic skin according to the present invention, a sound-sensing ability may be explained.

Figure 5E:
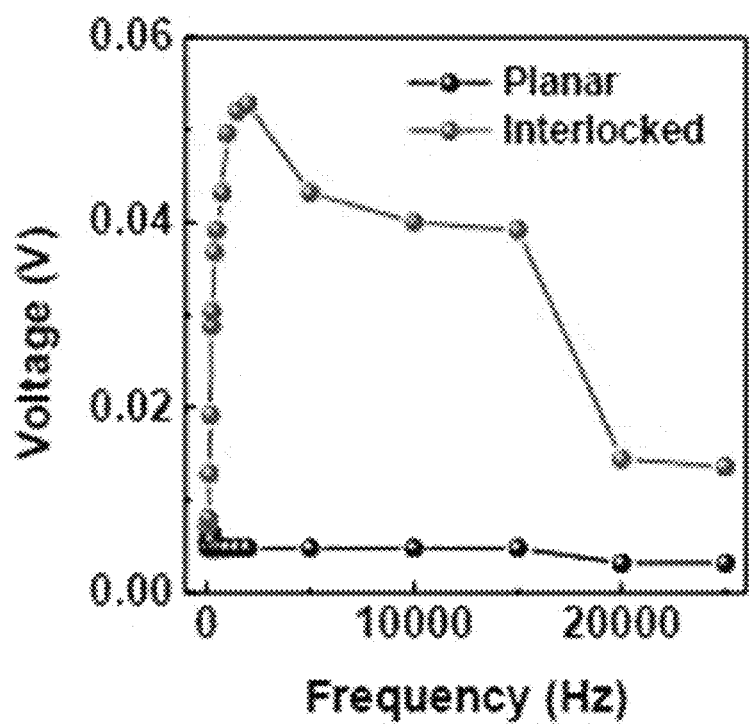

As illustrated in FIG. 5E, a piezoelectric voltage of the interlocked electronic skin increases in proportion to a frequency until the frequency reaches a maximum value of 2,000 Hz and gradually decreases after 2,000 Hz.

On the other hand, a piezoelectric voltage of a planar electronic skin does not significantly change according to a frequency change.

Figure 5F:
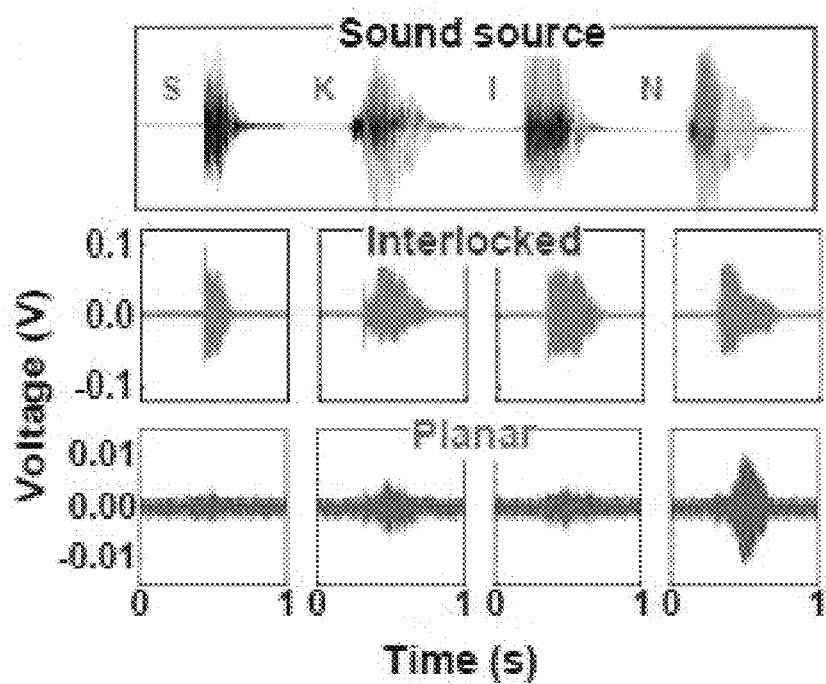

As illustrated in FIG. 5F, it can be seen that a piezoelectric voltage waveform responds with sounds of different alphabet letters such as S, K, I, and N from a speaker.

In order to describe the monitoring of an entire sentence of an acoustic waveform, a well-known Richard Feynman's speech entitled "There's plenty of room at the bottom" is output on the interlocked electronic skin through a commercial microphone.

Figure 5G:
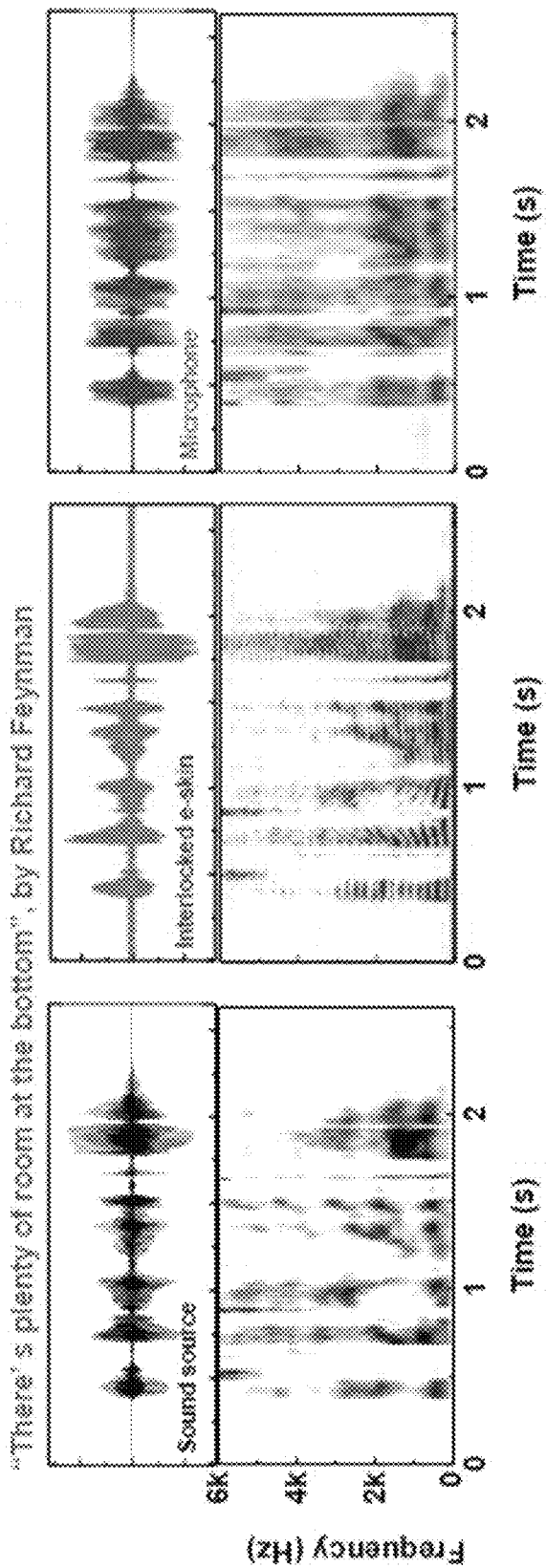

As illustrated in FIG. 5G, it can be seen that, in the interlocked electronic skin according to the present invention, a spectrogram corresponding to a position and an intensity of a piezoelectric voltage waveform according to time closely matches a spectrogram of an acoustic waveform of an acoustic sound of a sentence.

On the other hand, in the commercial microphone, it can be seen that a change of an acoustic waveform and a spectrogram of a sentence according to time may not be accurately observed.

A rapidly adapting piezoelectric electronic skin may allow spatial and temporal encoding of touch signals of a surface texture that are easy to recognize.

Figure 6A:
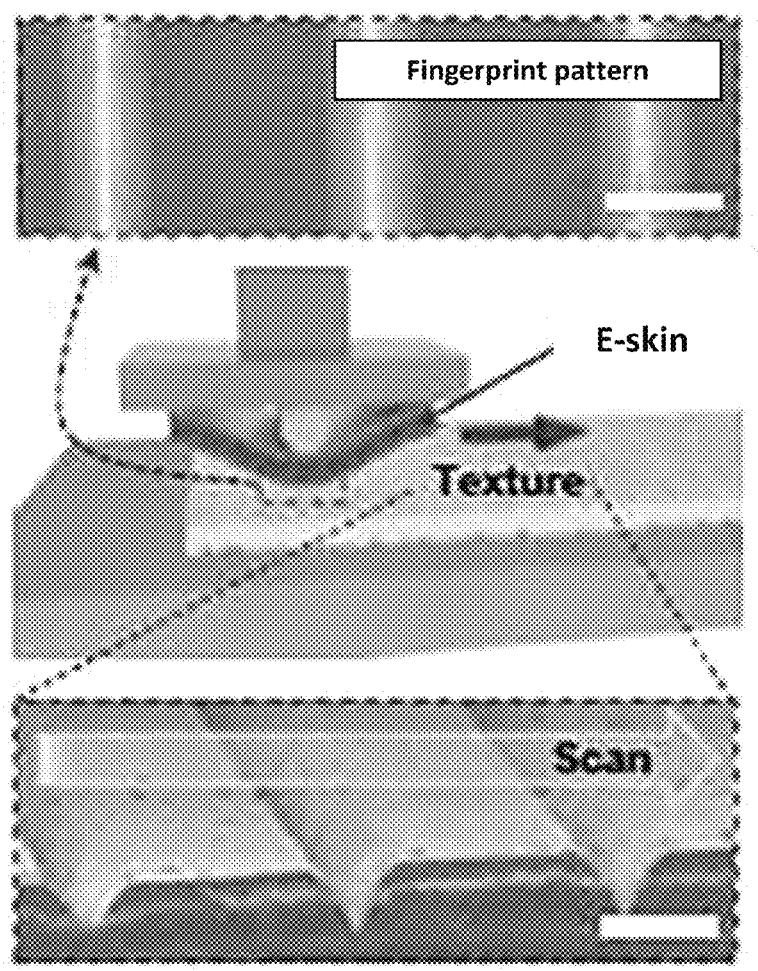
FIGS. 6A-6F illustrate diagrams for describing properties of a piezoelectric electronic skin having a fingerprint pattern to sense a texture.

To this end, the electronic skin is attached to a microstage, as illustrated in a middle portion of FIG. 6A, and scans through a surface texture at different scanning speeds, as illustrated in a lower portion of FIG. 6A.

Specifically, a ridge (a pitch of 470 μm and a width of 163 μm) parallel to a surface of the electronic skin is used to amplify a texture-induced vibration, as illustrated in an upper portion of FIG. 6A, to simulate a fingerprint pattern of a human hand.

Figure 6B:
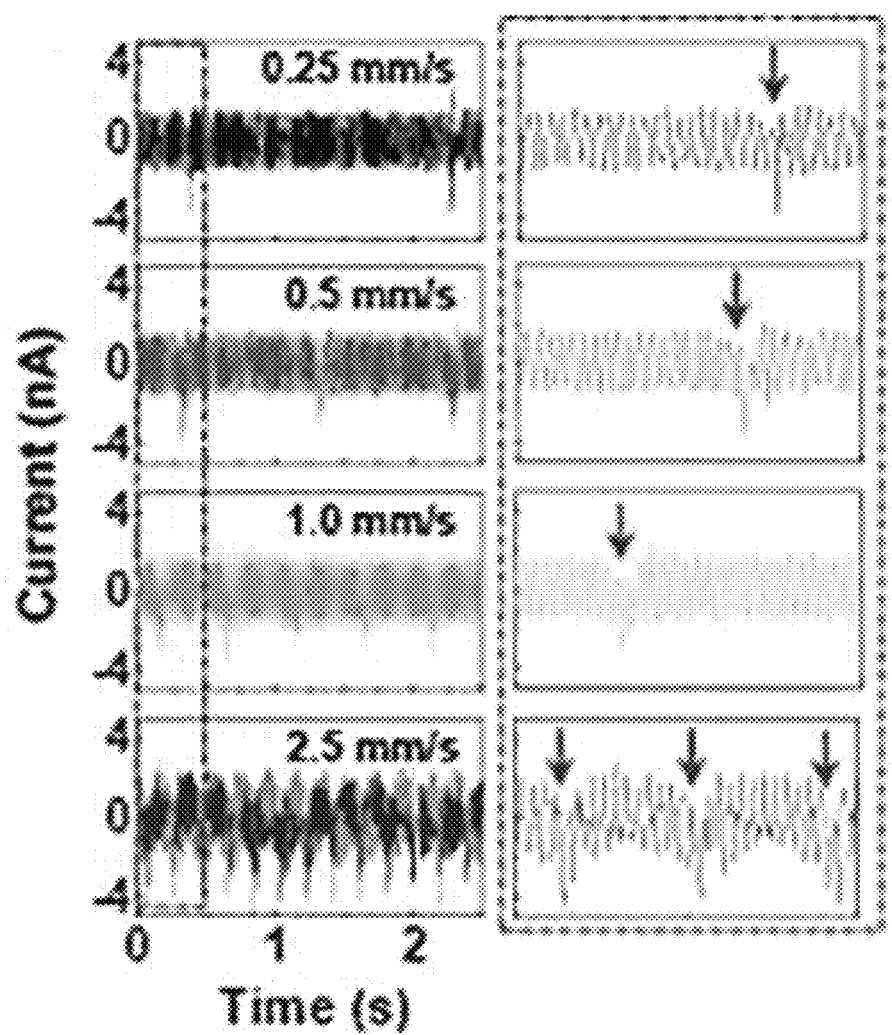

FIG. 6B illustrates a change of a piezoelectric current according to time when the interlocked electronic skin scans through a surface texture having a parallel line pattern at different scanning speeds (a range of 0.25 to 2.5 mm/s).

Figure 6C:
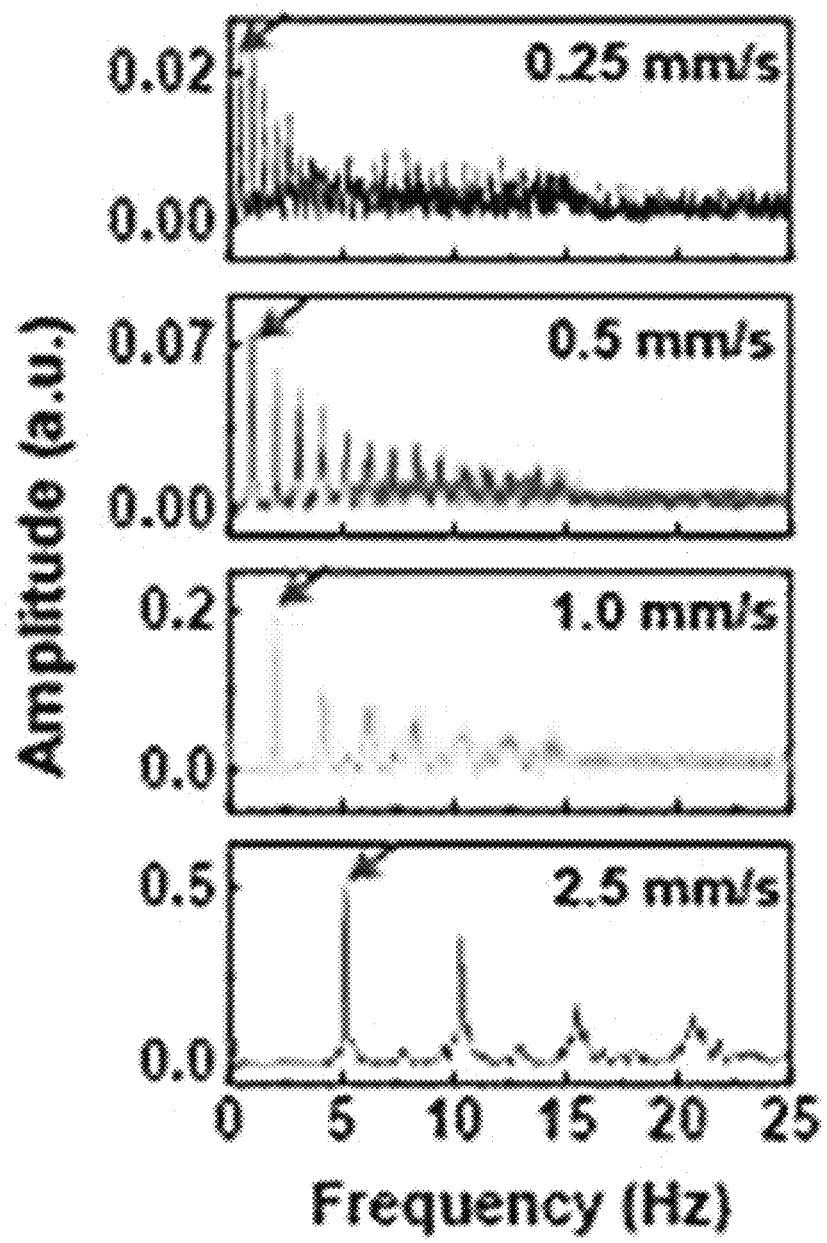

In FIG. 6C, a high-speed Fourier transform spectrum for the piezoelectric current signal indicates that there is a fundamental frequency (an arrow) related to a high frequency having each of the scanning speeds and a decreased amplitude.

Figure 6D:
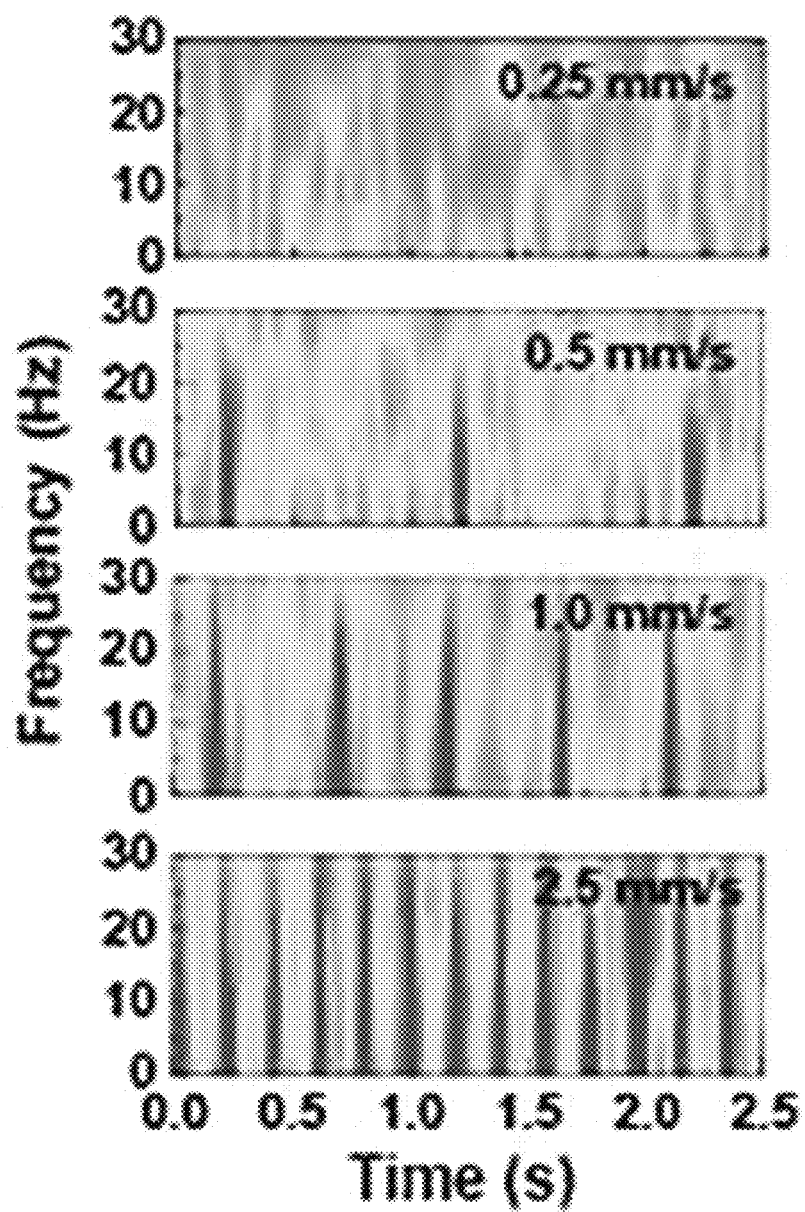

As illustrated in FIG. 6D, a short-time Fourier transform (STFT) for a current signal better illustrates a change of the piezoelectric current according to time.

Scanning for regular surface patterns induces periodic line patterns regarding time in a frequency range of 30 Hz or less, which increases with an increase of a scanning speed in the same time domain.

Figure 6E:
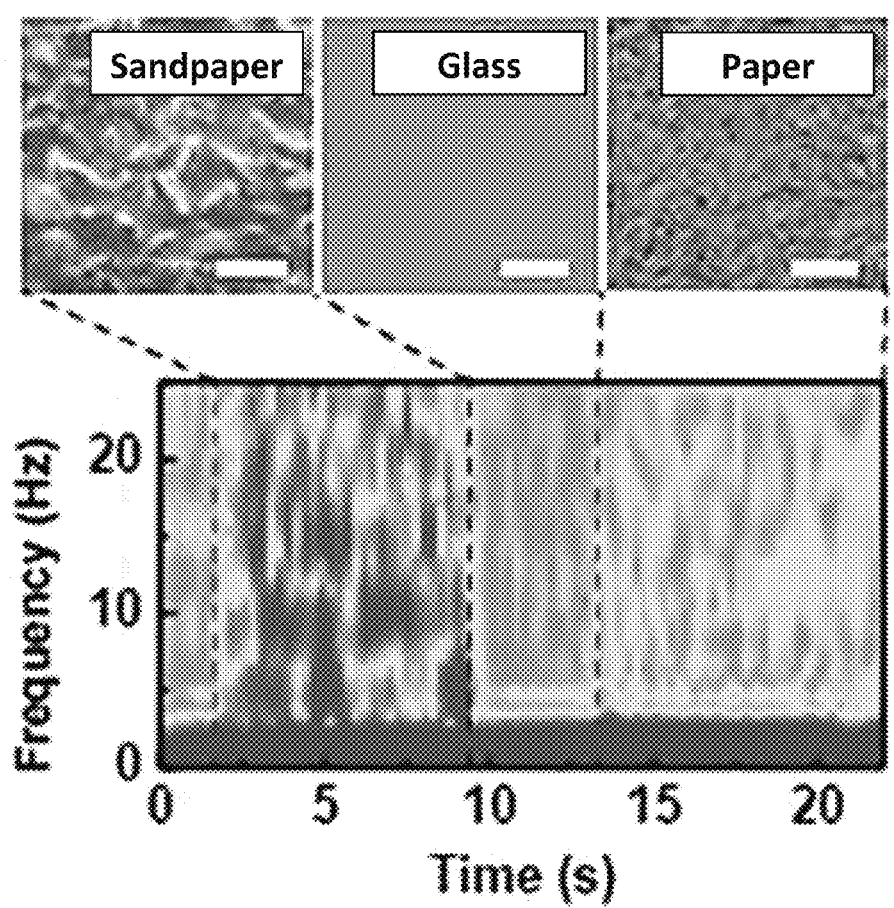

The interlocked artificial electronic skin having a fingerprint pattern according to the present invention may sense various surfaces having different roughnesses, such as sandpaper, glass, and paper, as illustrated in FIG. 6E.

Figure 6F:
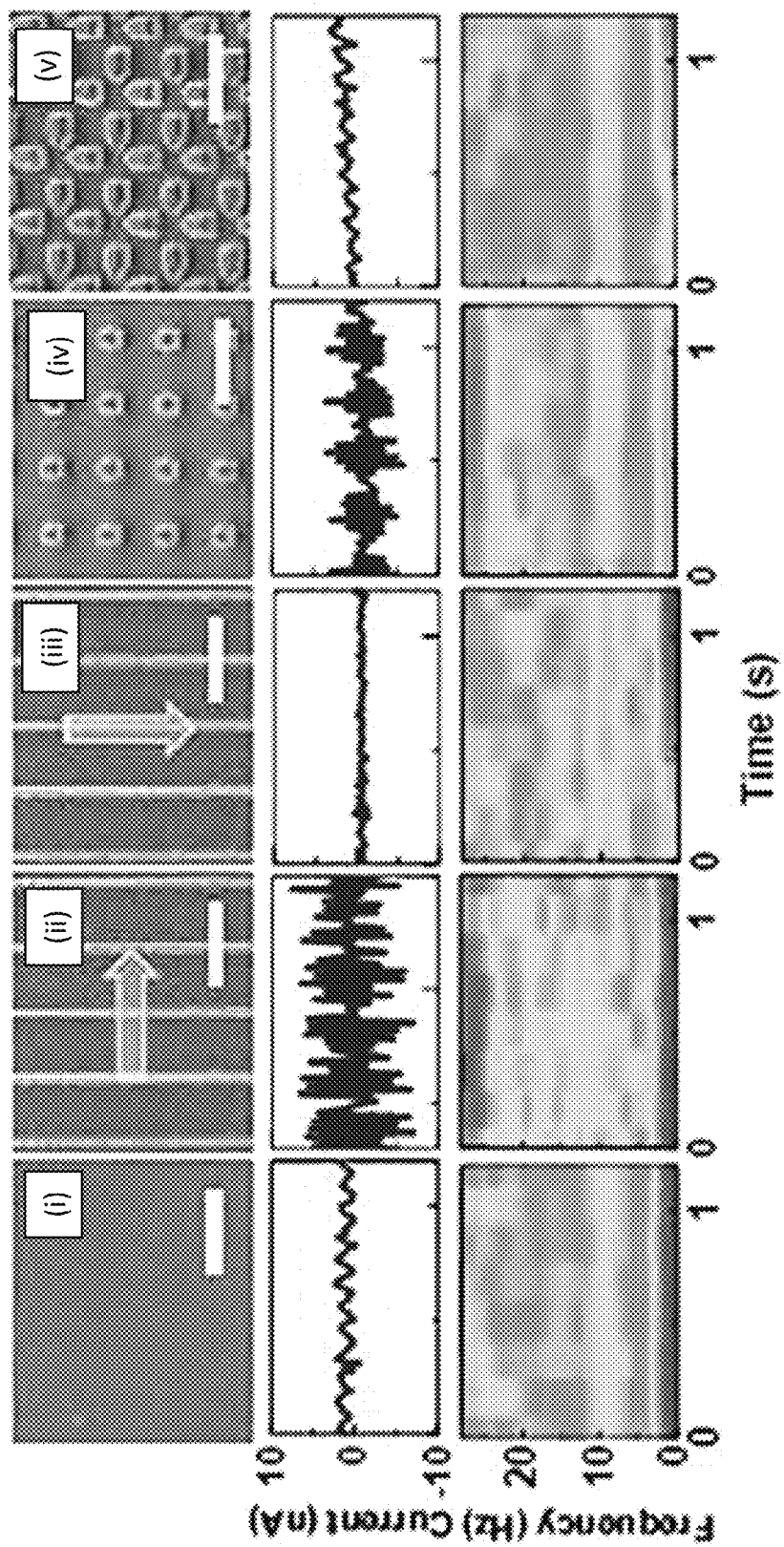

As illustrated in FIG. 6F, it can be seen that during detection of fine textures, the electronic skin scans a silicon substrate having different surface patterns and sizes (a line with a pitch size P=80 μm and a width W=10 μm, a rectangle with P=80 μm and W=20 μm, and a pentagon with P=90 μm and W=20 μm) at a scanning speed of 2.5 mm/s.

Scanning across a silicon line pattern in a vertical direction induces a periodic output current wave, as illustrated in a middle portion of FIG. 6F, and induces a proprietary frequency band near 30 Hz in a clearly recognizable STFT spectrogram, as illustrated in a lower portion of FIG. 6F, in comparison with a soft silicone surface (FIG. 6F(i)).

The 30 Hz frequency band observed at a scanning speed of 2.5 mm/s corresponds to a pitch of 83 um close to an internal ridge distance of 80 um.

On the other hand, scanning in a parallel direction (FIG. 6F(iii)) through the silicon line pattern cannot represent an important frequency band close to 30 Hz.

A square pattern (FIG. 6F(iv)) generates a frequency band close to 30 Hz similar to a band observed through scanning perpendicular to the line pattern.

On the other hand, scanning a pentagonal pattern (FIG. 6F(v)) without any continuous internal pattern spacing cannot represent any notable frequency band close to 30 Hz.

While the present invention has been described above with reference to specific embodiments and drawings, the present invention is not limited thereto. It should be clear to those skilled in the art that various modifications and alterations may be made without departing from the spirit and scope of the present invention and equivalents of the appended claims.

The invention claimed is:

1. An artificial electronic skin comprising: a lower electrode; a first layer laminated on the lower electrode; a hemispherical first micro dome formed on the first layer to stand upright; a second layer laminated on the first layer; a hemispherical second micro dome formed on a lower portion of the second layer which faces the first layer to be interlocked with the first micro dome; an upper electrode laminated on an upper end surface of the second layer; and a pattern layer laminated on an upper end surface of the upper electrode and configured to receive an external pressure applied thereto.

2. The artificial electronic skin of claim 1, wherein the first layer and the second layer are made of a composite material of polyvinylidene fluoride (PVDF) and reduced graphene oxide (rGO).

3. The artificial electronic skin of claim 1, wherein the pattern layer is configured with a pattern obtained by simulating a fingerprint.

4. The artificial electronic skin of claim 1, wherein, when water droplets having different temperatures are dropped onto the pattern layer the temperatures of the water droplets are sensed according to resistance values measured through the lower electrode and the upper electrode .

5. The artificial electronic skin of claim 4, wherein the resistance values and the temperatures of the water droplets are inversely proportional to each other.

6. The artificial electronic skin of claim 1, wherein, when water droplets having different temperatures are dropped onto the pattern layer, pressures applied by the water droplets are sensed according to resistance values measured through the lower electrode and the upper electrode.

7. The artificial electronic skin of claim 6, wherein the resistance values and the pressures applied by the water droplets are inversely proportional to each other.

8. The artificial electronic skin of claim 1, wherein, in a state of being encapsulated by a polyimide film and worn on a wrist, an intensity of a pulse transferred to the pattern layer through the lower electrode and the upper electrode is sensed while a skin temperature is measured by measuring a resistance value according to the intensity of the pulse.

9. The artificial electronic skin of claim 8, wherein the skin temperature and the resistance value are inversely proportional to each other.

10. The artificial electronic skin of claim 1, wherein, when sounds having different frequencies are transferred to the pattern layer, sound waves are detected through piezoelectric currents and voltages measured through the lower electrode and the upper electrode.

11. The artificial electronic skin of claim 1, wherein, when surfaces having different textures and patterns are scanned on the pattern layer, information on the surfaces is detected through piezoelectric currents and voltages measured through the lower electrode and the upper electrode.

* * * * *